US00PP33118P2

(12) United States Plant Patent
Konst

(10) Patent No.: US PP33,118 P2
(45) Date of Patent: Jun. 1, 2021

(54) ***ALSTROEMERIA* PLANT NAMED 'KONCACANDY'**

(50) Latin Name: *Alstroemeria hybrida*
Varietal Denomination: Koncacandy

(71) Applicant: Johannes Wilhelmus Maria Konst, Nieuwveen (NL)

(72) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 0 days.

(21) Appl. No.: 16/974,060

(22) Filed: Sep. 18, 2020

(51) Int. Cl.
*A01H 5/02* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
CPC ..... A01H 6/564; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Alstroemeria* plant named 'Koncacandy', characterized by its compact and mounding plant habit; sturdy and strong plants; vigorous growth habit and rapid growth rate; freely basal branching habit; numerous purplish pink and white-colored flowers with dark purplish red-colored stripes; and good garden performance.

2 Drawing Sheets

Botanical designation: *Alstroemeria hybrida.*
Cultivar denomination: 'KONCACANDY'.

STATEMENT REGARDING PRIOR DISCLOSURES BY INVENTOR/APPLICANT & ASSIGNEE

An European Community Plant Breeder's Rights application for the instant plant was filed by the Assignee, Könst Breeding B.V. of Nieuween, The Netherlands on Jul. 16, 2020, application number 2020/1727. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Alstroemeria* plant, botanically known as *Alstroemeria hybrida,* typically grown as a container-type garden *Alstroemeria* and hereinafter referred to by the name 'Koncacandy'.

The new *Alstroemeria* plant is a product of a planned breeding program conducted by the Inventor in Nieuwveen, The Netherlands. The objective of the breeding program is to create new compact container-type garden *Alstroemeria* plants that have an early and freely flowering habit with attractive leaf and flower coloration.

The new *Alstroemeria* plant originated from a cross-pollination made by the Inventor in Nieuwveen, The Netherlands in July, 2013 of a proprietary selection of *Alstroemeria hybrida* identified as code number 47911-2, not patented, as the female, or seed, parent with a proprietary selection of *Alstroemeria hybrida* identified as code number 52387-1, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands in September, 2014.

Asexual reproduction of the new *Alstroemeria* plant by in vitro rhizogenesis in a controlled greenhouse environment in Nieuwveen, The Netherlands since June, 2016 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncacandy'. These characteristics in combination distinguish 'Koncacandy' as a new and distinct *Alstroemeria* plant:

1. Compact and mounding plant habit.
2. Sturdy and strong plants.
3. Vigorous growth habit and rapid growth rate.
4. Freely basal branching habit.
5. Numerous purplish pink and white-colored flowers with dark purplish red-colored stripes.
6. Good garden performance.

Plants of the new *Alstroemeria* can be compared to plants of the female parent selection in flower color as plants of the new *Alstroemeria* have purplish pink and white-colored flowers whereas plants of the female parent selection have reddish pink-colored flowers. In addition, plants of the new *Alstroemeria* are more compact than plants of the female parent selection.

Plants of the new *Alstroemeria* can be compared to plants of the male parent selection in flower color as plants of the new *Alstroemeria* have purplish pink and white-colored flowers whereas plants of the male parent selection have dark salmon pink-colored flowers. In addition, plants of the new *Alstroemeria* are more compact than plants of the male parent selection.

Plants of the new *Alstroemeria* can be compared to plants of the *Alstroemeria hybrida* 'Koncavanti', disclosed in U.S. Plant Pat. No. 22,283. In side-by-side comparisons, plants of the new *Alstroemeria* differ from plants of 'Koncavanti' in the following characteristics:

1. Plants of the new *Alstroemeria* are shorter and not as broad as plants of 'Koncavanti'.
2. Plants of the new *Alstroemeria* have shorter leaves than plants of 'Koncavanti'.
3. Plants of the new *Alstroemeria* are more freely flowering than plants of 'Koncavanti'.
4. Plants of the new *Alstroemeria* flower earlier than plants of 'Koncavanti'.
5. Plants of the new *Alstroemeria* have purplish pink and white-colored flowers with dark purplish red-colored stripes whereas plants of 'Koncavanti' have pink-colored flowers with distinct dark purple-colored stripes.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Koncacandy' grown in container.

The photograph on the second sheet is a close-up view of a typical flowering plant of 'Koncacandy'.

DETAILED BOTANICAL DESCRIPTION

The aforementioned photographs and following observations and measurements describe plants of the new *Alstroemeria* grown during the spring and summer in 19-cm containers in a glass-covered greenhouse in Nieuwveen, The Netherlands and under cultural practices typical of commercial container-type *Alstroemeria* production. During the production of the plants, day temperatures ranged from 9° C. to 35° C. and night temperatures ranged from 6° C. to 20° C. Plants were twelve weeks old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Koncacandy'.

Parentage:

*Female, or seed, parent.*—Proprietary selection of *Alstroemeria hybrida* identified as code number 47911-2, not patented.

*Male or pollen parent.*—Proprietary selection of *Alstroemeria hybrida* identified as code number 52387-1, not patented.

Propagation:

*Type.*—In vitro rhizogenesis.

*Root description.*—Thick, fleshy; typically white in color, actual color of the roots is dependent on substrate composition, water quality, fertilizers, substrate temperature and physiological age of roots.

*Rooting habit.*—Freely branching; dense.

*Rhizome description.*—Shape: Elongate; rounded. Length: About 3.7 cm. Diameter: About 1.2 cm. Texture: Smooth. Color: Close to 162D.

Plant description:

*Plant and growth habit.*—Perennial garden plant; compact and mounded; freely branching habit, bushy appearance; sturdy and strong plants; vigorous growth habit and rapid growth rate.

*Plant height.*—About 25 cm.

*Plant diameter* (*area of spread*).—About 32 cm.

Stem description:

*Aspect.*—Mostly upright.

*Internode length.*—About 0.7 cm to 1.8 cm.

*Strength.*—Strong, sturdy.

*Texture.*—Smooth, glabrous.

*Color.*—Close to 144A slightly tinged with close to 183A.

Leaf description:

*Arrangement.*—Alternate; below the peduncle, arranged in a single whorl; leaves sessile; about 10 to 16 leaves per lateral branch.

*Length.*—About 3.3 cm to 7.4 cm.

*Width.*—About 0.8 cm to 2.4 cm.

*Shape.*—Lanceolate.

*Apex.*—Acute.

*Base.*—Attenuate.

*Margin.*—Entire.

*Texture and luster, upper and lower surfaces.*—Smooth, glabrous; matte.

*Venation pattern.*—Parallel.

*Color.*—Developing leaves, upper surface: Close to 139B. Developing leaves, lower surface: Close to 138A. Fully expanded leaves, upper surface: Close to 137A; venation, close to 144A. Fully expanded leaves, lower surface: Close to 138A; venation, close to 143A.

Flower description:

*Flower type and habit.*—Single cup-shaped flowers arranged in compound umbels; flowers face upright to outwardly; freely flowering habit with up to 15 flowers developing per inflorescence and about 30 to 105 flowers developing per plant during the flowering season.

*Natural flowering season.*—Flowering continuous from the late spring until the autumn in The Netherlands; early-flowering habit, plants begin flowering about 10 to 16 weeks after stem initiation.

*Fragrance.*—None detected.

*Flower longevity on the plant.*—About one to three weeks, longevity is temperature-dependent; flowers not persistent.

*Flower longevity as a cut flower.*—About one to two weeks, longevity is temperature-dependent; flowers not persistent.

*Flower buds.*—Length: About 5.2 cm. Diameter: About 1.4 cm. Shape: Ovoid. Color: Close to 63B; venation, close to N134B.

*Umbel height.*—About 8.5 cm to 10 cm.

*Umbel diameter.*—About 13.5 cm to 15 cm.

*Flower diameter.*—About 6.1 cm.

*Flower depth (height).*—About 6.4 cm.

*Perianth.*—Arrangement: Six arranged in two whorls, each whorl with two lateral and one median segments. Size, inner perianth: Length, lateral segments: About 6.8 cm. Width, lateral segments: About 1.8 cm. Length, median segment: About 5.7 cm. Width, median segment: About 1.8 cm. Size, outer perianth: Length, lateral segments: About 6.4 cm. Width, lateral segments: About 3.5 cm. Length, median segment: About 6.4 cm. Width, median segment: About 3.5 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Emarginate, wishbone-shaped. Base, inner and outer perianths, lateral and median segments: Attenuate. Margin, inner perianth, lateral and median segments: Entire. Margin, outer perianth, lateral and median segments: Proximally, entire; distally, serrulate. Texture and luster, inner and outer perianths, lateral and median segments: Smooth, glabrous; matte, dull. Color, inner perianth, lateral segments: When opening and fully opened, upper surface: Proximally, close to 62C; center, close to 155C; distally, close to 63C; large stripes, close to 187A and smaller distal stripes, close to 60C; color does not change with development. When opening and fully opened, lower surface: Proximally, close to N34D; center, close to 63D and 155C; distally, close to 63B with small spot, close to 60D, and venation, close to 137D; large stripes from upper surface visible, close to 187A; color does not change with development. Color, inner perianth, median segment: When opening and fully opened, upper surface: Proximally, close to 63D; distally, close to 63C; large stripes, close to 187A and smaller distal stripes, close to 60C; color does not change with development. When opening and fully opened, lower surface: Close to 63D; distally with spot, close to 60D; large stripes from upper surface visible, close to 187A; color does not change with development. Color, outer perianth, lateral segments: When opening and fully opened, upper surface: Close to N57C; towards the base, close to 62C; distally with spot, close to 60C; color does not change with development. When opening and fully opened, lower surface: Close to N57D; distally with spot and venation, close to 137D; color does not change with development. Color, outer perianth, median segment: When opening and fully opened, upper surface: Close to N57C; towards the base, close to 62C; distally with spot, close to 60C; color does not change with development. When opening and fully opened, lower surface: Close to N57D; distally with spot and venation, close to 137D; color does not change with development.

*Pedicels.*—Length: About 0.5 cm to 2.2 cm. Diameter: About 3 mm. Strength: Strong. Angle: About 15° from vertical. Texture: Smooth, glabrous. Color, upper and lower surfaces: Close to 144A strongly tinged with close to 183A.

*Reproductive organs.*—Stamens: Quantity per flower: Six. Anther shape: Oval. Anther size: About 2 mm by 8 mm. Anther color: Close to 199B. Pollen amount: Abundant. Pollen color: Close to N199A. Pistils: Quantity per flower: One. Pistil length: About 4.4 cm. Style length: About 3.5 cm. Style color: Close to between 59D and 58A. Stigma color: Close to 58A. Ovary color: Close to 144A strongly tinged with close to 183A.

*Fruits.*—Quantity per flower: One. Length: About 1 cm. Diameter: About 8 mm. Color: Close to 144A strongly tinged with close to 183A.

*Seeds.*—To date, seed development has not been observed on plants of the new *Alstroemeria.*

Pathogen & pest resistance: To date, plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncacandy' as illustrated and described.

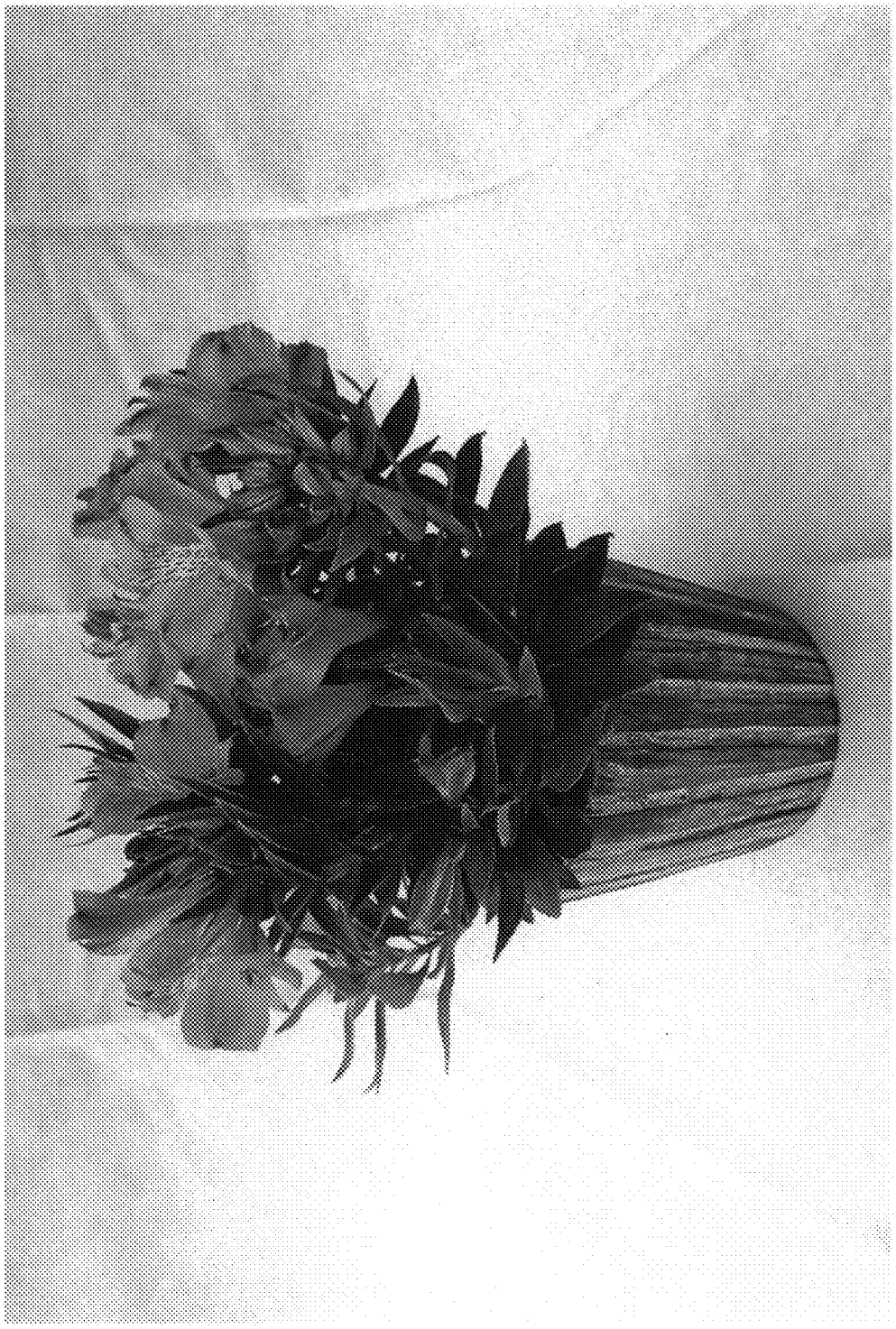

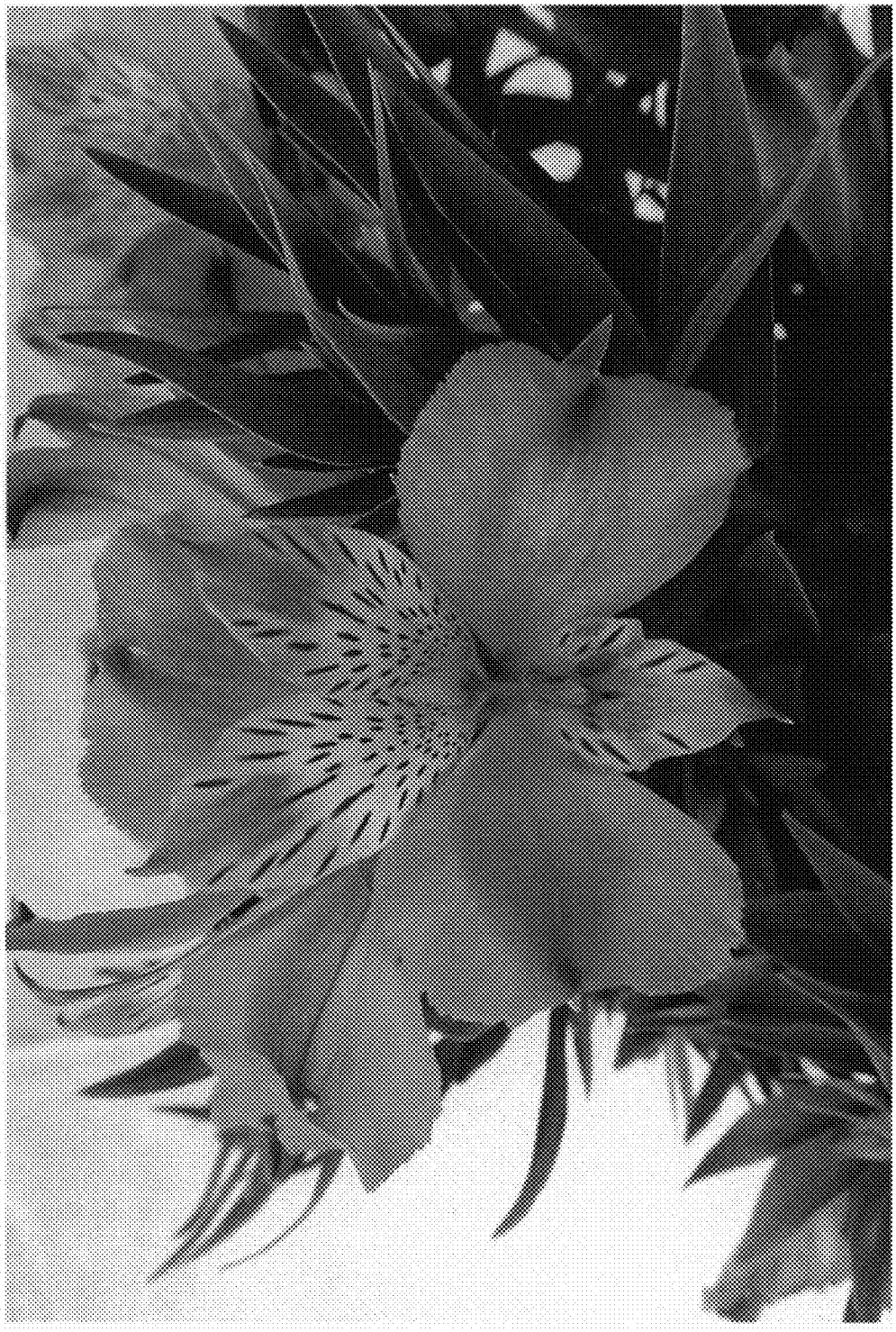

* * * * *